United States Patent
Teppke

(10) Patent No.: US 8,246,905 B2
(45) Date of Patent: Aug. 21, 2012

(54) METHOD FOR DISINFECTING A MICROTOME CRYOSTAT

(75) Inventor: Dieter Teppke, Schwetzingen (DE)

(73) Assignee: MICROM International GmbH, Walldorf (DE)

( * ) Notice: Subject to any disclaimer, the term of this patent is extended or adjusted under 35 U.S.C. 154(b) by 1176 days.

(21) Appl. No.: 12/078,580

(22) Filed: Apr. 2, 2008

(65) Prior Publication Data

US 2008/0181814 A1    Jul. 31, 2008

Related U.S. Application Data

(63) Continuation of application No. 10/543,195, filed as application No. PCT/EP03/13267 on Nov. 26, 2003, now abandoned.

(30) Foreign Application Priority Data

Feb. 1, 2003    (DE) .................................. 103 03 989

(51) Int. Cl.
     *A61L 2/00*          (2006.01)
     *A61L 2/18*          (2006.01)
     *A61L 9/00*          (2006.01)
     *A61L 2/04*          (2006.01)
     *A61L 2/20*          (2006.01)
     *A61L 11/00*        (2006.01)
     *C23F 11/00*        (2006.01)

(52) U.S. Cl. ................... 422/28; 422/1; 422/31; 422/33; 422/292; 422/295; 422/300; 422/307

(58) Field of Classification Search ............... 422/28, 422/292, 295, 297, 298, 299, 300, 1, 31, 422/33; 62/51.1
See application file for complete search history.

(56) References Cited

U.S. PATENT DOCUMENTS

| | | | | |
|---|---|---|---|---|
| 4,909,999 A | * | 3/1990 | Cummings et al. | ........... 422/298 |
| 5,122,344 A | * | 6/1992 | Schmoegner | ................. 422/111 |
| 5,974,811 A | * | 11/1999 | Heid et al. | ......................... 62/78 |
| 2003/0143110 A1 | * | 7/2003 | Kritzler et al. | .................. 422/29 |

FOREIGN PATENT DOCUMENTS

| DE | 3202627 A1 | * | 8/1983 |
|---|---|---|---|
| FR | 2705587 | * | 12/1994 |

OTHER PUBLICATIONS

FR 2705587—English translation.*
DE 3202627—English machine translation of claims.*
DE 3202627—English translation of Abstract.*
FR 2705587—English translation, 2011.*
DE 3202627—English machine translation of claims, 2011.*
DE 3202627—English translation of Abstract, 1983.*

* cited by examiner

*Primary Examiner* — Regina M. Yoo
(74) *Attorney, Agent, or Firm* — Paul Vincent

(57) ABSTRACT

A method for disinfecting a microtome cryostat (1) comprises a defrosting phase (11), provision (13) of a vaporous disinfection agent (2) which acts upon the closed cryostat chamber (3) and a period of time (14) during which said disinfection agent (2) acts, and having an associated device for carrying out the method. According to the invention, fast and effective disinfection and rapid restarting of a microtome cryostat (1) is possible with secure drying, the temperature difference ($\Delta T_1$, $\Delta T_2$) being produced after the period of time (14) in the cryostat chamber (3) whereupon the precipitated disinfection agent (2) is removed (18) to a cold area.

17 Claims, 2 Drawing Sheets

METHOD FOR DISINFECTING A MICROTOME CRYOSTAT

This application is a continuation of Ser. No. 10/543,195, filed Jul. 22, 2005 now abandoned, which is the national stage of PCT/EP2003/013267 filed on Nov. 26, 2003 and claims Paris Convention priority of DE 103 03 989.9 filed Feb. 1, 2003 the entire disclosures of which are hereby incorporated by reference.

BACKGROUND OF THE INVENTION

The invention concerns a method for disinfecting a microtome cryostat, comprising a defrosting phase, provision of a vaporous disinfectant which acts upon the closed cryostat chamber, and a period of time during which the disinfectant is effective. An associated device for disinfecting a microtome cryostat, comprises a microtome in a cryostat chamber, a refrigerator, a means for providing a vaporous disinfectant, and a disinfectant controller means to set an effective time after a defrosting phase.

Disinfection is necessary to protect the operating personnel since microtomes are used for cutting tissue samples which are often infected with germs. Spraying is problematic, in particular, for cryostat microtomes, since the moisture must be removed from the cryostat chamber. Residual moisture on a cryostat microtome freezes after refrigeration for the next working step. Guidances etc. may thereby freeze with the consequence that the microtome is inoperable, or liquid disinfectant, e.g. a highly concentrated alcohol solution, remains in the chamber and causes further problems, even danger of explosion.

US 2002/0139124 A1 proposes a solution to this problem by disinfection with ozone. This is, however, disadvantageous, since ozone is highly corrosive and damages the surfaces via oxidation. A further disadvantage is that residual ozone is difficult to remove, is poisonous and highly inflammable, and can partially escape from the device even during the disinfecting phase, which could endanger the operating personnel.

The company leaflet "AS 600 Cryotome" (ANGLIA SCIENTIFIC) proposes another solution for decontamination using UV radiation. Disadvantageously, the UV radiation does not reach the shadow regions. Moreover, the UV radiation cannot penetrate deeply enough into cutting waste or sample residues nor into microscopically small depressions in metal surfaces. This method of decontamination is therefore unsatisfactory.

A proposal of the above-mentioned type is disclosed in the company leaflets "AS 620 Cryotome" and "AS 620 Cryotome Instruction Manual" (ANGLIA SCIENTIFIC Instruments LTD). A formalin dispenser is thereby heated and the closed cryostat chamber is charged with formalin vapor. The above-mentioned problem of residual moisture in the cryostat and, in particular, on the microtome, also occurs in this case with the consequence that the device must be left open for a relatively long time to dry. Disinfectant thereby escapes which should be prevented for health reasons and due to possible annoyance caused by bad smell. Moreover, the device is inoperable for a relatively long time or is not completely dried.

It is therefore the underlying purpose of the invention to further develop a method and associated device of the above-mentioned type to ensure rapid and effective disinfection to permit as fast a renewed operation of a microtome cryostat as possible as well as complete drying thereof.

SUMMARY OF THE INVENTION

This object is achieved in accordance with the inventive method in that a temperature difference is generated in the cryostat chamber after the effective time and disinfectant deposited in the colder region is discharged. The associated controller is designed to generate that temperature difference through heating and/or cooling, and a collecting device is disposed in the colder region to remove deposited disinfectant.

With the present invention, disinfectant and moisture deposit in a colder region after disinfection and are discharged from there in a controlled manner, thereby permitting fast drying and rapid renewed operation while subjecting critical regions of the device, such as the microtome, to particularly effective drying by heating instead of cooling them. This prevents formation of ice during renewed cooling for the next working step which would otherwise impair or prevent further operation. In particular, the device is ready for reliable reuse within a short time after disinfection.

The most different means can be used as disinfectant, mainly in the form of aqueous solutions, e.g. glutaraldehyde, benzalconium chloride, formalin and didecyl dimethyl ammonium chloride.

The temperature difference can be generated both by cooling as well as by heating of a region. It is thereby advantageous to use existing cooling or heating devices. The temperature of the refrigerator of the cryostat may be reduced below 0° C. in a cooling phase after the effective time until at least the majority of the disinfectant has deposited on the refrigerator followed by defrosting of the refrigerator to discharge the disinfectant from the cryostat chamber using a collecting device. A collecting device of this type is usually disposed below the refrigerator to be able to remove the defrosted dew or defrosted ice liquids from the cryostat chamber.

Another possibility is to heat the microtome after the effective time. Due to such heating, the disinfectant, e.g. the disinfecting solution, is transferred from the microtome to colder parts of the device with the result that the microtome is dried for the subsequent cooling phase. The temperature difference can, of course, be obtained through cooling as well as heating, wherein a combination of the two above-mentioned measures is preferred. The colder regions within the cryostat chamber are preferably selected such that the deposited disinfectant or moisture can be easily collected and discharged.

In any event, the heating temperature is preferably considerably higher than the surrounding temperature of the cryostat in order to completely dry the microtome.

To also achieve maximum effective disinfection, the invention proposes blowing the vaporous disinfectant into the cryostat chamber. This forced convection causes uniform wetting of all components. The disinfectant can be vaporized through a heater, wherein vaporization is preferably effected through ultrasound which permits generation of a uniform aerosol without separating the phases of the substances of the disinfectant, thereby providing uniform disinfection. The disinfectant may, of course, also be present in the form of vapor.

The cryostat is preferably heated after the defrosting phase to at least the surrounding temperature. This heating is preferably followed by a temperature balancing time to ensure that all components have the same temperature and are subjected to uniform disinfection during the effective time of the disinfectant. Different heaters may be used for heating, wherein a heater installed in the microtome is preferred. Heating via the microtome prevents thawing thereof and thereby dilution of the solvent during the actual subsequent disinfection during the effective time, which provides excellent disinfection of the microtome.

The cutting waste should be mechanically removed before introduction of the vaporous disinfectant. This may be effected manually or the cutting waste may be suctioned to thereby prevent residual contamination in the cryostat chamber by the cutting waste.

Moreover, vaporous disinfectant may be suctioned into a suction system for disinfection thereof. Suctioning disinfects tubes, filters, pump and blocking devices of the suction system.

Further developments and embodiments of the device may correspond to the further developments and embodiments of the method and vice versa, wherein the above-mentioned advantages can be achieved in each case.

In a further development of the invention, the controller is designed to reduce the temperature of the refrigerator of the cryostat below 0° C. in a cooling phase after the effective time until at least the majority of the disinfectant has deposited on the refrigerator, and the refrigerator is subsequently thawed to discharge the disinfectant from the cryostat chamber using the collecting means.

Alternatively or additionally, the microtome may comprise a heater and the controller may be designed to initiate heating of the microtome after the effective time thereby completely drying the microtome as already described in connection with the method.

The refrigerator also advantageously comprises a heater with the controller being designed to switch on the heater to accelerate thawing. The disinfectant and moisture condensed on the refrigerator can thereby be easily liquefied and discharged, ensuring rapid reoperation of the device.

The means for providing a vaporous disinfectant preferably comprises a blower for introducing the vaporous disinfectant into the cryostat chamber to achieve forced convection into the cryostat chamber with uniform distribution of the disinfectant. The means for vaporizing the disinfectant is preferably provided with an ultrasound actuator to realize the above-mentioned atomization of the disinfectant without phase separation. The means for generating the vaporous disinfectant is preferably supplied with disinfectant from a supply container. A valve may be provided to controller the liquid level of the disinfectant in the means for generating the vaporous disinfectant.

The invention is explained below with reference to the figures of the drawing showing examples.

DESCRIPTION OF THE PREFERRED EMBODIMENT

Figure 1:
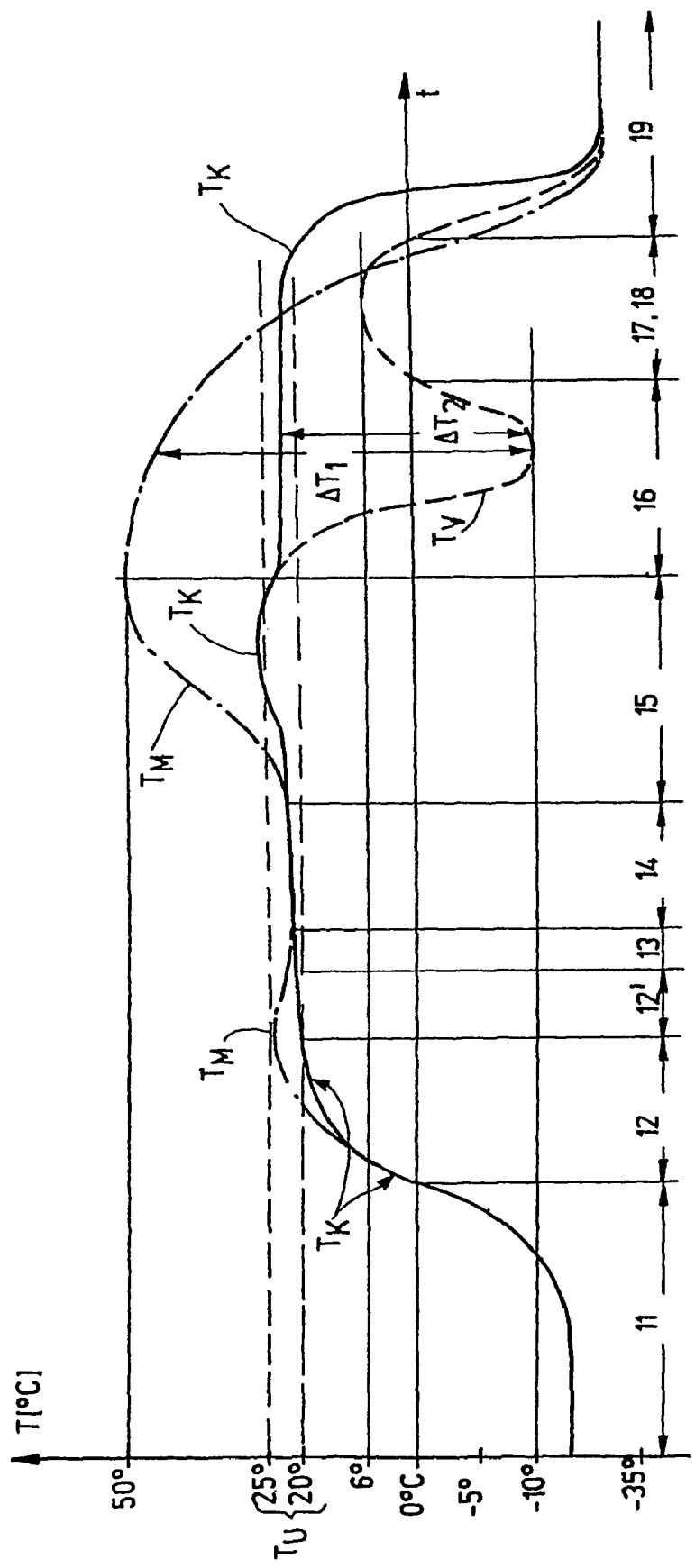
FIG. 1 shows an exemplary view of the temperature dependences and method steps of an inventive method.

FIG. 1 shows examples of possible temperature dependences of the inventive method, wherein the temperatures T in 0° C. are plotted against time t and possible method steps 11 through 19 are shown.

Starting from an operational temperature of the microtome of between −5° C. and −35° C., a defrosting phase 11 is initiated with heating 12 to at least the surrounding temperature $T_U$ which is within a range from 20 to 25° C. This process is preferably accelerated by operating the heater 7 of the microtome 6, wherein heating via the microtome 6 is advantageous in that the latter does not thaw. For this reason, the disinfectant 2 cannot be diluted by the dew during subsequent disinfection. In view of the device features, reference is made to FIG. 2.

Due to the microtome heater, the temperature $T_M$ of the microtome 6 increases faster than the temperature $T_K$ of the cryostat chamber 3. Heating 12 is therefore preferably followed by a temperature balancing time 12'. When all components have reached approximately the same temperature, a vaporous disinfectant 2 is provided 13 which is blown into the cryostat chamber 3.

When all components have been uniformly wetted with disinfectant 2, heating 15 of the microtome 6 by the microtome heater 7 is initiated after lapse of an effective time 14, thereby further increasing the temperature $T_M$ of the microtome 6, e.g. to 50° C. to transfer moisture and disinfectant from the microtome 6 to the colder parts of the cryostat chamber 3. To cause precise sublimation of the disinfectant on the refrigerator 4 of the cryostat 1, the cryostat 1 is cooled below 0° C. in a cooling phase 16, preferably to a region of −10° C. Temperature differences $\Delta T_1$ and $\Delta T_2$ are thereby generated, wherein $\Delta T_1$ is the difference between the temperature $T_M$ of the microtome 6 and of the temperature $T_V$ of the refrigerator 4, and $\Delta T_2$ is the difference between the temperature $T_K$ of the cryostat chamber 3 and the temperature $T_V$ of the refrigerator 4. In consequence thereof, the disinfectant 2 and moisture on the refrigerator 4 are condensed on the refrigerator 4 and deposit there in the form of dew and ice. A defrosting phase 17 of the refrigerator 4 is then initiated during which the thawed liquid is discharged. The thawed liquid is discharged 18 using a collecting device 5 which guides the thawed liquid out of the cryostat chamber 3. Thawing 17 of the refrigerator 4 is suitably supported by a heater 10 of the refrigerator 4, wherein the latter is heated e.g. to +6° C. When the thawed liquid has been discharged, the cryostat chamber 3 and, in particular, the microtome 6 are dry. Cooling can be repeated for reoperation 19 to bring the microtome cryostat 1 again to its operating temperature for new object processing.

Figure 2:
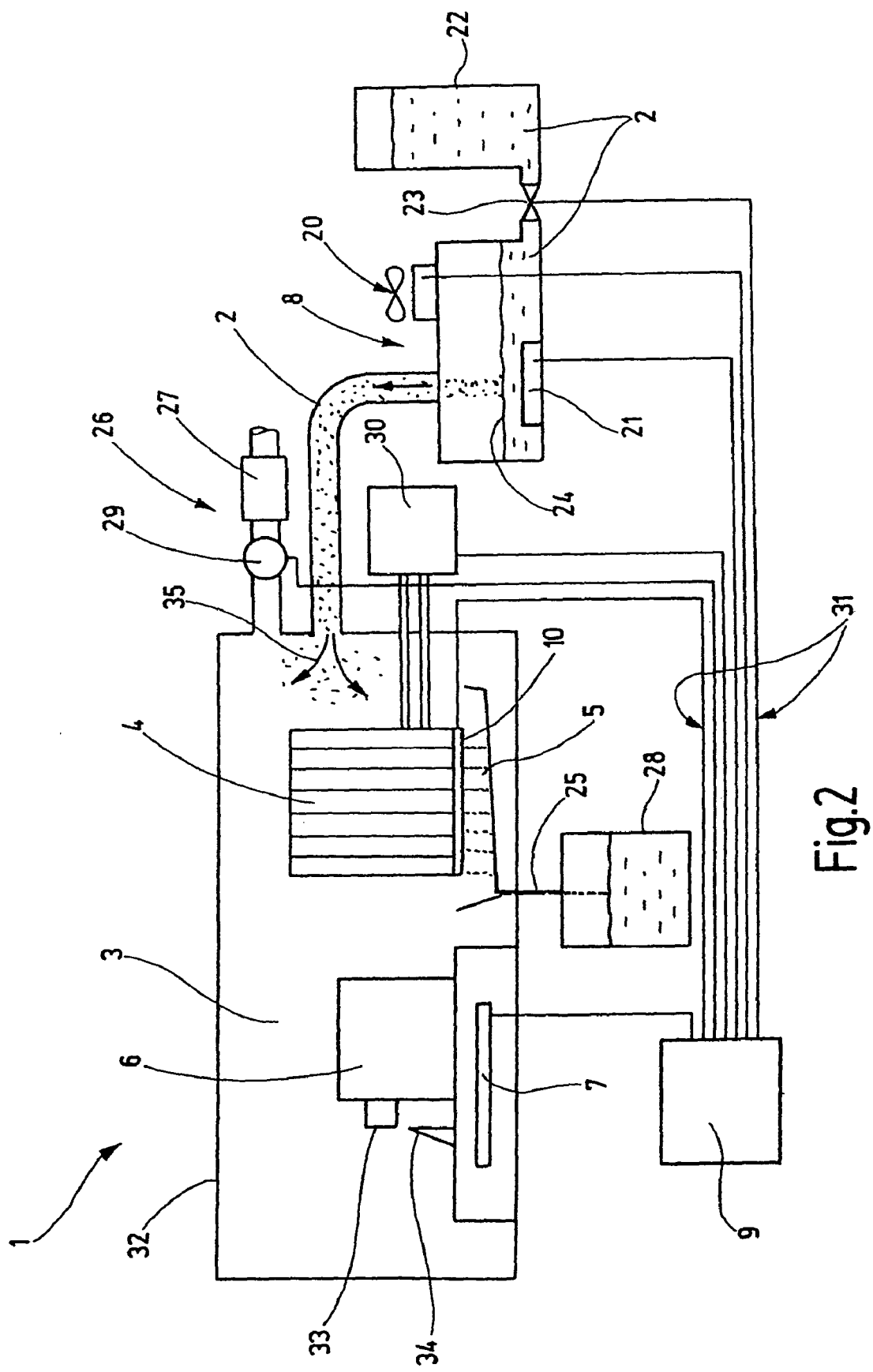
FIG. 2 shows an embodiment of an inventive microtome cryostat.

FIG. 2 shows an embodiment of an inventive microtome cryostat 1. The microtome cryostat 1 consists of a cooled housing which surrounds a cryostat chamber 3 and can be opened via an opening 32. The cryostat chamber 3 contains a microtome 6 including an object carrier 33 and a knife 34 for producing the cuts. The cryostat chamber 3 is cooled using a refrigerator 4, e.g. a vaporizer, which is connected to a coolant supply 30. The microtome 6 as well as the refrigerator 4 are provided with heaters 7 and 10 to provide rapid thawing and heating. A collecting means 5 is provided below the refrigerator 4 which is designed e.g. as drip pan which discharges thawed liquid from the cryostat chamber 3 into a supply container 28 via an outlet 25.

Moreover, a means 8 for providing a vaporous disinfectant 2 blows the evaporated disinfectant 2 via a pipe into the cryostat chamber 3 in the direction of the arrows 35. Towards this end, a blower 20 and an ultrasound actuator 21 are provided to generate the aerosol from the liquid disinfectant 2. A supply container 22 and a valve 23 thereby ensure that the liquid level 24 of the disinfectant 2 in the means 8 is always maintained.

In accordance with the invention, a controller 9 is connected to the heater 7 of the microtome 6, to the heater 10 of the refrigerator 4, to the ultrasound actuator 21, the blower 20 and the coolant supply 30 of the refrigerator 4 via connecting lines 31. The controller 9 may furthermore be connected to sensors (not shown) for detecting the temperature, air moisture, etc. to ensure effective controller of the described temperatures and drying processes. Connection to a ventilator 29 of a suction system 26 and to a valve 23 and further functional elements is also possible.

The connecting lines 31 provide controller 9 of the temperature dependences $T_K$, $T_M$ and $T_V$ (FIG. 1) and of the method steps 11 through 19 by controlling the heaters 7 and/or 10 and cooling using the refrigerator 4. The controller 19 also controllers the supply 13 of the vaporous disinfectant 2 via the means 8.

The controller 9 can also initiate suctioning of vaporous disinfectant 2 into the suction system 26 for disinfecting e.g. the ventilator 29, the pipes and the filter 27 located therein.

The illustrated temperature dependences $T_K$, $T_M$ and $T_V$ and working steps 11 through 19 of FIG. 1 and the device features of FIG. 2 are only examples. The temperature differences $\Delta T_1$ and $\Delta T_2$ for the deposit of disinfectant 2 and moisture and the discharge thereof are essential. An alternative design of the heaters or alternative generation of temperature differences within the cryostat chamber 3 are also possible, e.g. only through heating or only through cooling, or the time sequence may be different, wherein e.g. method steps 11 through 19 could partially overlap.

LIST OF REFERENCE NUMERALS 1 microtome cryostat (cryostat)
2 disinfectant
3 cryostat chamber
4 refrigerator (of the cryostat) e.g. vaporizer
5 collecting device
6 microtome
7 microtome heater
8 means for providing a vaporous disinfectant
9 controller
10 heater of the refrigerator
11 defrosting phase
12 heating to at least surrounding temperature
12' temperature balancing time
13 providing a vaporous disinfectant
14 effective time of the disinfectant
15 heating the microtome
16 cooling refrigerator
17 thawing refrigerator
18 discharging the thawed liquid
19 cooling for reoperation
20 blower
21 ultrasound actuator
22 supply container for disinfectant
23 valve
24 liquid level
25 discharge
26 suction system
27 filter
28 supply container for thawed liquid
29 ventilator
30 coolant supply of the refrigerator (vaporizer)
31 connecting lines for control
32 opening of the cryostat chamber
33 object carrier
34 knife
34 arrows: blowing in vaporous disinfectant
T temperature in ° C.
t time
$\Delta T_1$ temperature difference between refrigerator and microtome
$\Delta T_2$ temperature difference between refrigerator and cryostat chamber
$T_U$ surrounding temperature of the cryostat
$T_K$ temperature of the cryostat chamber
$T_M$ temperature of the microtome
$T_V$ temperature of the refrigerator (vaporizer)

I claim:

1. A method for disinfecting a cryostat, the cryostat having a microtome disposed in a closed cryostat chamber, the method comprising the steps of:
   a) subjecting the cryostat to a defrosting phase;
   b) introducing a vaporous disinfectant into the closed cryostat chamber;
   c) waiting an effective time for action of the disinfectant;
   d) generating a temperature difference in the closed cryostat chamber following step c); and
   e) discharging the disinfectant deposited in a colder region of the closed cryostat chamber in response to step d), wherein, following step c), a temperature of a cryostat refrigerator is reduced to below 0° C. in a cooling phase until at least a majority of the disinfectant has deposited on the refrigerator, the refrigerator being subsequently thawed to discharge the disinfectant from the cryostat chamber with the assistance of a collecting device.

2. The method of claim 1, wherein the microtome is heated after step c).

3. The method of claim 2, wherein a heating temperature clearly exceeds a surrounding temperature of the cryostat.

4. The method of claim 1, wherein the vaporous disinfectant is blown into the cryostat chamber.

5. The method of claim 1, wherein the disinfectant is evaporated using ultrasound.

6. The method of claim 1, wherein the cryostat is heated to at least a surrounding temperature following step a).

7. The method of claim 6, wherein a heating period is followed by a temperature balancing time.

8. The method of claim 6, wherein the heating is effected using a microtome heater.

9. The method of claim 1, wherein a cutting waste is mechanically removed prior to step b).

10. The method of claim 9, wherein the cutting waste is suctioned off.

11. The method of claim 1, wherein the vaporous disinfectant is suctioned into a suction system to also disinfect same.

12. The method of claim 1, wherein the cooling is effected by means of the refrigerator and a controller regulates introduction of disinfectant and waiting of the effective time, wherein the controller also generates the temperature difference in the cryostat chamber of step d) through heating and/or cooling, wherein the collecting device is disposed in the colder region to remove deposited disinfectant.

13. The method of claim 12, wherein the microtome has a heater and said heater is structured to heat the microtome after the effective time of step c).

14. The method of claim 12, wherein the refrigerator comprises a heater and the controller switches on the heater to accelerate thawing.

15. The method of claim 12, wherein a disinfectant supply container holds the disinfectant.

16. The method of claim 15, further comprising a valve for controlling a disinfectant level.

17. The method of claim 12, wherein the collecting device discharges liquid, dripping from the refrigerator, out of the cryostat chamber via an outlet.

* * * * *